(12) United States Patent
Shiratani

(10) Patent No.: US 10,491,813 B2
(45) Date of Patent: Nov. 26, 2019

(54) IMAGE PROCESSING APPARATUS AND IMAGE PROCESSING METHOD

(71) Applicant: OLYMPUS CORPORATION, Hachioji-shi, Tokyo (JP)

(72) Inventor: Fumiyuki Shiratani, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/412,936

(22) Filed: May 15, 2019

(65) Prior Publication Data

US 2019/0268538 A1 Aug. 29, 2019

Related U.S. Application Data

(63) Continuation of application No. PCT/JP2016/086408, filed on Dec. 7, 2016.

(51) Int. Cl.
*H04N 5/232* (2006.01)
*A61B 1/00* (2006.01)
(Continued)

(52) U.S. Cl.
CPC ..... *H04N 5/23229* (2013.01); *A61B 1/00009* (2013.01); *G06K 9/3233* (2013.01); *G06T 7/11* (2017.01); *G06T 2207/20084* (2013.01)

(58) Field of Classification Search
CPC .... H04N 5/23229; G06K 9/3233; G06T 7/11; G06T 2207/20084; A61B 1/00009
See application file for complete search history.

(56) References Cited

U.S. PATENT DOCUMENTS 7,551,800 B2 * 6/2009 Corcoran ............... G06K 9/40
382/254
7,599,576 B2 * 10/2009 Baldwin ............ G06K 9/2036
382/141
(Continued)

FOREIGN PATENT DOCUMENTS

EP  1437083 A1  7/2004
JP  H10210454 A  8/1998
(Continued)

OTHER PUBLICATIONS

International Search Report (ISR) dated Feb. 21, 2017 issued in International Application No. PCT/JP2016/086408.
(Continued)

*Primary Examiner* — Chiawei Chen
(74) *Attorney, Agent, or Firm* — Holtz, Holtz & Volek PC

(57) ABSTRACT

An image processing apparatus includes a processor. The processor is configured to: obtain a presumption result by presuming an operation state of a user who performs an operation while the user observes an image obtained by picking up an image of a subject; perform processing for correcting a specular reflection region included in the image obtained by picking up the image of the subject; and when detecting, based on the presumption result, that a first operation related to search for a desired object in the subject is performed, perform control for causing the image in which the specular reflection region is maintained to be outputted as an observation image, and when detecting that a second operation related to discrimination of the desired object found in the subject is performed, perform control for causing the image in which the specular reflection region is corrected to be outputted as an observation image.

7 Claims, 7 Drawing Sheets

(51) Int. Cl.
 *G06T 7/11* (2017.01)
 *G06K 9/32* (2006.01)

(56) References Cited

U.S. PATENT DOCUMENTS

| | | | | |
|---|---|---|---|---|
| 8,073,286 | B2* | 12/2011 | David | G06K 9/40 |
| | | | | 382/254 |
| 9,513,218 | B2* | 12/2016 | Ohba | G01N 21/55 |
| 10,375,279 | B2* | 8/2019 | Ilic | H04N 5/2173 |
| 2005/0010082 | A1 | 1/2005 | Nishimura et al. | |
| 2008/0069433 | A1* | 3/2008 | Corcoran | G06K 9/40 |
| | | | | 382/149 |
| 2008/0075385 | A1* | 3/2008 | David | G06K 9/40 |
| | | | | 382/275 |
| 2011/0268350 | A1* | 11/2011 | Tsukada | G06T 1/00 |
| | | | | 382/154 |
| 2011/0274351 | A1* | 11/2011 | Tsukada | H04N 1/62 |
| | | | | 382/167 |
| 2015/0055821 | A1* | 2/2015 | Fotland | G06K 9/3241 |
| | | | | 382/103 |
| 2016/0100146 | A1* | 4/2016 | Sakai | H04N 5/2351 |
| | | | | 348/169 |
| 2017/0023888 | A1* | 1/2017 | Shibasaki | G03G 15/1615 |
| 2018/0045635 | A1* | 2/2018 | Debreczeny | G01N 21/51 |

FOREIGN PATENT DOCUMENTS

| | | |
|---|---|---|
| JP | 2003093328 A | 4/2003 |
| JP | 2012050601 A | 3/2012 |
| WO | 03026497 A1 | 4/2003 |
| WO | 2016181720 A1 | 11/2016 |

OTHER PUBLICATIONS

Written Opinion dated Feb. 21, 2017 issued in International Application No. PCT/JP2016/086408.

* cited by examiner

IMAGE PROCESSING APPARATUS AND IMAGE PROCESSING METHOD

CROSS REFERENCE TO RELATED APPLICATION

This application is a continuation application of PCT/JP2016/086408 filed on Dec. 7, 2016, the entire contents of which are incorporated herein by this reference.

BACKGROUND OF THE INVENTION

1. Field of the Invention

The present invention relates to an image processing apparatus and an image processing method.

2. Description of the Related Art

In endoscope observation, specular reflection can occur due to a short distance between a light exit face of an optical member that outputs illumination light to an outside of an endoscope and an object illuminated by the illumination light, and the like.

With respect to the problem, for example, Japanese Patent Application Laid-Open Publication No. 10-210454 discloses a technology relating to an image processing apparatus that performs image processing on an endoscope image obtained by an endoscope and is configured to remove, as an ineffective region, a region having inappropriate data in calculation of an IHb amount, such as a halation part caused by specular reflection.

SUMMARY OF THE INVENTION

An image processing apparatus according to an aspect of the present invention includes a processor. The processor is configured to: obtain a presumption result by presuming an operation state of a user who performs an operation while the user observes an image obtained by picking up an image of a subject; perform processing for correcting a specular reflection region included in the image obtained by picking up the image of the subject; and when detecting, based on the presumption result, that a first operation related to search for a desired object in the subject is performed, perform control for causing the image in which the specular reflection region is maintained to be outputted as an observation image, and when detecting that a second operation related to discrimination of the desired object found in the subject is performed, perform control for causing the image in which the specular reflection region is corrected to be outputted as an observation image.

An image processing method according to another aspect of the present invention includes: obtaining a presumption result by presuming an operation state of a user who performs an operation while the user observes an image obtained by picking up an image of a subject; performing processing for correcting a specular reflection region included in the image obtained by picking up the image of the subject; and when detecting, based on the presumption result, that a first operation related to search for a desired object in the subject is performed, performing control for causing the image in which the specular reflection region is maintained to be outputted as an observation image, and when detecting that a second operation related to discrimination of the desired object found in the subject is per- formed, performing control for causing the image in which the specular reflection region is corrected to be outputted as an observation image.

DETAILED DESCRIPTION OF THE PREFERRED EMBODIMENTS

Hereinafter, embodiments of the present invention will be described with reference to drawings.

First Embodiment

Figure 1:
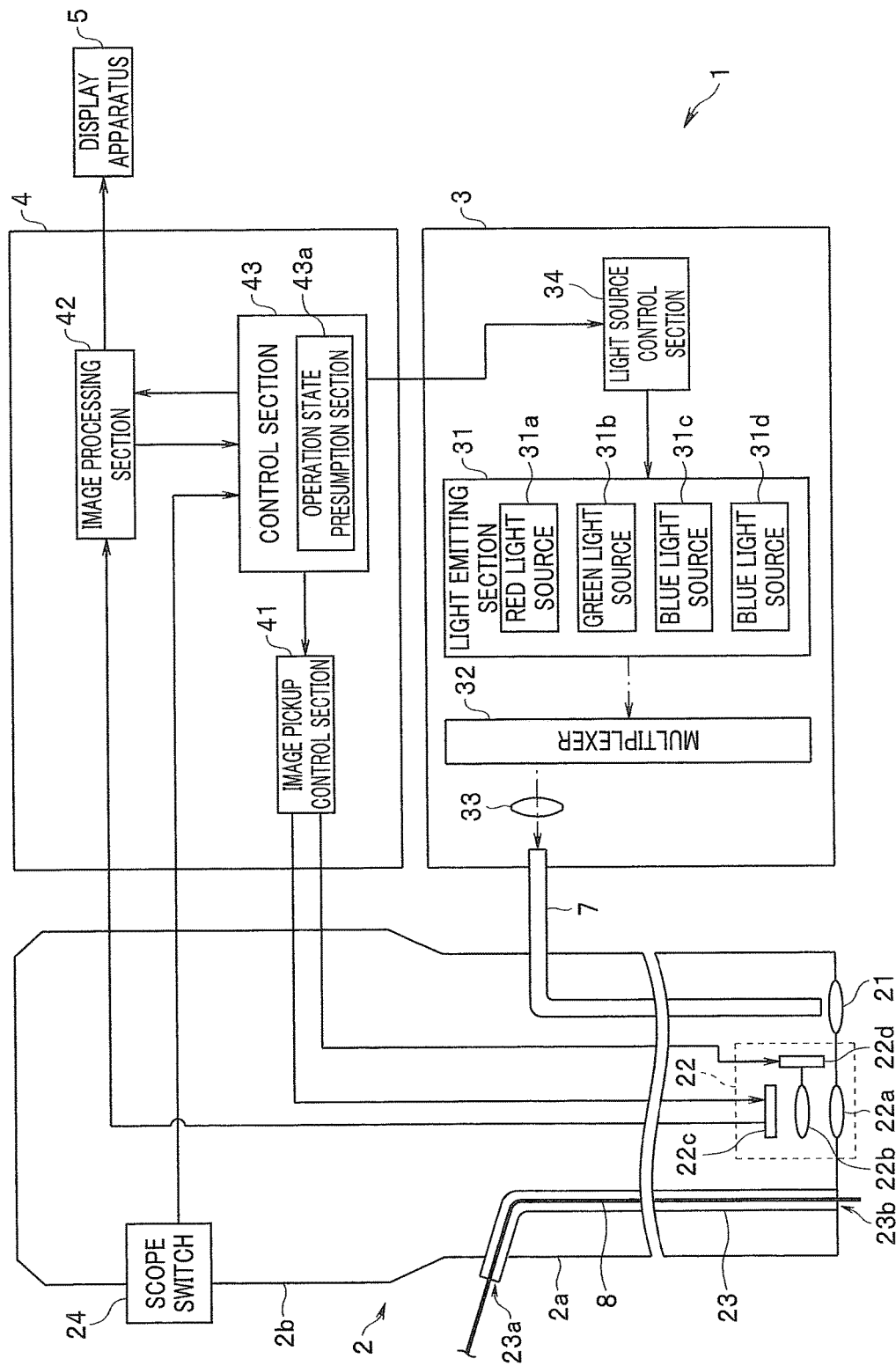
FIG. 1 is a diagram showing a configuration of main sections of an endoscope system including an image processing apparatus according to an embodiment.
Figure 2:
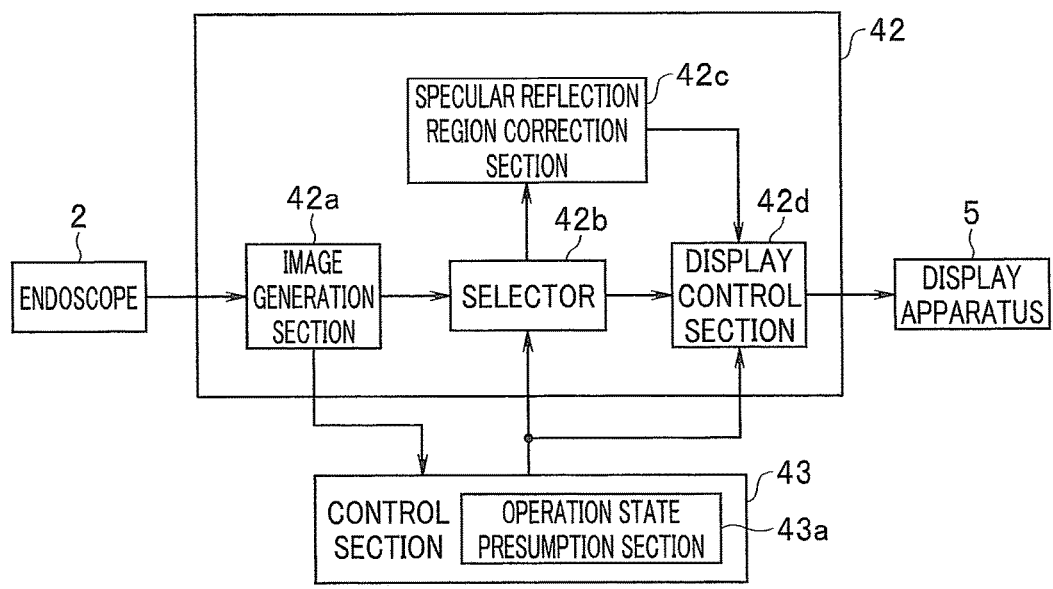
FIG. 2 is a diagram for describing an example of a configuration of an image processing section according to a first embodiment.

FIGS. 1 and 2 relate to a first embodiment of the present invention.

As shown in FIG. 1, an endoscope system 1 includes an endoscope 2 configured to be insertable into a body cavity of a subject, which is a living body, to pick up an image of an object such as a body tissue existing in the body cavity, and to output an image pickup signal, a light source apparatus 3 configured to supply illumination light for illuminating the object to the endoscope 2, a processor 4 configured to generate and output an observation image corresponding to the image pickup signal outputted from the endoscope 2, and a display apparatus 5 capable of displaying the observation image and the like outputted from the processor 4. FIG. 1 is a diagram showing a configuration of main sections of the endoscope system including an image processing apparatus according to the embodiment.

The endoscope 2 is configured with an insertion portion 2a formed in an elongated shape insertable into the body cavity of the subject, and an operation portion 2b provided on a proximal end side of the insertion portion 2a.

An inside of the insertion portion 2a allows insertion of a light guide 7 configured to transmit the illumination light supplied from the light source apparatus 3 to a distal end portion of the insertion portion 2a. At the distal end portion of the insertion portion 2a, an illumination lens 21 configured to apply the illumination light outputted through the light guide 7 onto the object, and an image pickup portion 22 configured to pick up an image of reflection light (hereinafter, also referred to as return light) coming from the object illuminated by the illumination light and to output an image pickup signal are provided. A treatment instrument channel 23 configured to allow insertion of an elongated treatment instrument 8 used for move, removal, and the like of a lesion existing in the body cavity of the subject is provided within the insertion portion 2a. In other words, the treatment instrument 8 includes a function as an observation assist instrument used when the subject is observed by using the endoscope 2.

The image pickup portion 22 includes an objective lens 22a, a focusing lens 22b, an image pickup device 22c, and a lens drive mechanism 22d.

The objective lens 22a is configured to faun an optical image corresponding to return light coming from the object illuminated by the illumination light outputted via the illumination lens 21.

The focusing lens 22b is configured to focus the optical image formed by the objective lens 22a. The focusing lens 22b is configured to be movable along an optical axis in accordance with an action of the lens drive mechanism 22d.

The image pickup device 22c is configured with, for example, a CCD or a CMOS. The image pickup device 22c is configured with a plurality of pixels for performing photoelectric conversion of the optical image focused by the focusing lens 22b and picking up an image, and a color filter provided on an image pickup face where the plurality of pixels are arranged two-dimensionally. Note that the color filter is formed by arranging, for example, minute R (red), G (green), and B (blue) filters at locations corresponding to the individual pixels of the image pickup device 22c in a Bayer arrangement (in a checkboard pattern). The image pickup device 22c is configured to be driven in response to an image pickup device drive signal outputted from the processor 4, to generate an image pickup signal by picking up the optical image focused by the focusing lens 22b, and to output the generated image pickup signal to the processor 4.

The lens drive mechanism 22d is configured to be able to perform an action for moving the focusing lens 22b within a predetermined movable range between a light exit face of the objective lens 22a and the image pickup face of the image pickup device 22c, based on a lens drive signal outputted from the processor 4.

The treatment instrument channel 23 includes an insertion opening 23a that is an opening provided at a proximal end portion of the insertion portion 2a, and a protrusion opening 23b that is an opening provided at the distal end portion of the insertion portion 2a. The treatment instrument channel 23 is formed in such a manner as to include a tubular shape that allows the elongated treatment instrument 8 inserted from the insertion opening 23a to protrude from the protrusion opening 23b.

The operation portion 2b is configured in such a manner as to include a shape that can be grasped and operated by a user. On the operation portion 2b, a scope switch 24 configured with switches that can issue an instruction according to an input operation of the user to the processor 4 is provided.

More specifically, the scope switch 24 is provided with, for example, an observation mode setting switch (not shown) that can issue to the processor 4 an instruction for setting an observation mode of the endoscope system 1 to either a white light observation mode or a narrowband light observation mode. The scope switch 24 is provided with, for example, an optical zoom switch (not shown) that can issue to the processor 4 an instruction related to optical magnification. The scope switch 24 is provided with, for example, a polyp diagnosis assist switch (not shown) that can issue to the processor 4 an instruction for setting on or off a function for assisting diagnosis (hereinafter, also referred to as the diagnosis assist function) of a polyp, which is an abnormality existing within the body cavity of the subject.

The light source apparatus 3 includes a light emitting section 31, a multiplexer 32, a condensing lens 33, and a light source control section 34.

The light emitting section 31 includes a red light source 31a, a green light source 31b, and blue light sources 31c and 31d.

The red light source 31a is configured with, for example, a red LED. The red light source 31a is configured to emit R light that is, for example, narrowband red light with a center wavelength set in a red region close to 600 nm. The red light source 31a is configured to switch into a lighted state or an unlighted state in accordance with control by the light source control section 34. In the lighted state, the red light source 31a is configured to emit the R light with an intensity or a light amount according to control by the light source control section 34.

The green light source 31b is configured with, for example, a green LED. The green light source 31b is configured to emit G light that is, for example, narrowband green light with a center wavelength set in a green region close to 540 nm. The green light source 31b is configured to switch into a lighted state or an unlighted state in accordance with control by the light source control section 34. In the lighted state, the green light source 31b is configured to emit the G light with an intensity or a light amount according to control by the light source control section 34.

The blue light source 31c is configured with, for example, a blue LED. The blue light source 31c is configured to emit BL light that is, for example, narrowband blue light with a center wavelength set in a blue region close to 460 nm. The blue light source 31c is configured to switch into a lighted state or an unlighted state in accordance with control by the light source control section 34. In the lighted state, the blue light source 31c is configured to emit the BL light with an intensity or a light amount according to control by the light source control section 34.

The blue light source 31d is configured with, for example, a blue LED. The blue light source 31d is configured to emit BS light that is, for example, narrowband blue light with a center wavelength set in a blue region close to 410 nm. The blue light source 31d is configured to switch into a lighted state or an unlighted state in accordance with control by the light source control section 34. In the lighted state, the blue light source 31d is configured to emit the BS light with an intensity or a light amount according to control by the light source control section 34.

The multiplexer 32 is configured to be able to combine each light emitted from the light emitting section 31 and to allow the combined light to enter the condensing lens 33.

The condensing lens 33 is configured to condense the light entering via the multiplexer 32 and to allow the light to exit to the light guide 7.

The light source control section 34 is configured with, for example, a light source control circuit. The light source control section 34 is configured to perform control on each light source of the light emitting section 31 in accordance with a system control signal outputted from the processor 4.

The processor 4 includes an image pickup control section 41, an image processing section 42, and a control section 43.

The image pickup control section 41 is configured with, for example, an image pickup control circuit. The image pickup control section 41 is configured to generate and output an image pickup device drive signal for driving the image pickup device 22c in accordance with a system control signal outputted from the control section 43. The image pickup control section 41 is configured to generate and output a lens drive signal for driving the lens drive mechanism 22d in accordance with a system control signal outputted from the control section 43.

The image processing section 42 is configured with, for example, an image processing circuit. The image processing section 42 includes, for example, an image generation section 42a, a selector 42b, a specular reflection region correction section 42c, and a display control section 42d as shown in FIG. 2. FIG. 2 is a diagram for describing an example of a configuration of the image processing section according to the first embodiment.

The image generation section 42a is configured to generate an image based on an image pickup signal outputted from the endoscope 2 and to output the generated image to the selector 42b and the control section 43.

The selector 42b is configured to perform an action for setting an output destination of the image outputted from the image generation section 42a to either the specular reflection region correction section 42c or the display control section 42d, in accordance with a system control signal outputted from the control section 43.

The specular reflection region correction section 42c is configured to perform processing for extracting a specular reflection region from the image outputted via the selector 42b and correcting the extracted specular reflection region. The specular reflection region correction section 42c is configured to output the image in which the specular reflection region is corrected through the processing, to the display control section 42d.

More specifically, for example, the specular reflection region correction section 42c performs processing of extracting, as the specular reflection region, a region including one or more pixels each having a pixel value equal to or higher than a predetermined threshold value, based on the image inputted via the selector 42b. The specular reflection region correction section 42c performs processing of interpolating between the pixel value of each pixel included in the specular reflection region extracted as described above, by using pixel values around the specular reflection region.

Note that the specular reflection region correction section 42c is not limited to be configured to correct the specular reflection region by the method as illustrated above, the specular reflection region correction section 42c may correct the specular reflection region by using a publicly known method disclosed in Japanese Patent Application Laid-Open Publication No. 10-210454 and others.

The display control section 42d is configured to perform an action for outputting, as an observation image, the image outputted from either the image generation section 42a or the specular reflection region correction section 42c to the display apparatus 5, in accordance with a system control signal outputted from the control section 43.

The control section 43 is configured with, for example, a control circuit such as a CPU. The control section 43 is configured to generate and output a system control signal for controlling each of the light source control section 34, the image pickup control section 41, and the image processing section 42, based on an instruction from the scope switch 24.

More specifically, for example, the control section 43 is configured to generate a system control signal for causing illumination light according to the observation mode of the endoscope system 1 to be supplied to the endoscope 2, and to output the system control signal to the light source control section 34, based on an instruction from the observation mode setting switch of the scope switch 24. For example, the control section 43 is configured to generate a system control signal for causing the focusing lens 22b to be moved and placed at a location according to an observation magnification of the image pickup portion 22, and to output the system control signal to the image pickup control section 41, based on an instruction from the optical zoom switch of the scope switch 24.

The control section 43 includes an operation state presumption section 43a configured to obtain a presumption result by presuming, based on an instruction from the scope switch 24 and/or the image outputted from the image processing section 42, an operation state of the user who performs an operation while observing an image (endoscope image) obtained by picking up the image of the subject by using the endoscope 2. The control section 43 is configured to be able to generate and output a system control signal for controlling actions of the selector 42b and the display control section 42d, based on an instruction from the polyp diagnosis assist switch of the scope switch 24 and the presumption result obtained by the operation state presumption section 43a.

Next, concrete actions and the like of the endoscope system 1 according to the present embodiment will be described.

After the user connects each section and portion of the endoscope system 1 and turns on a power supply, the user makes instructions for setting the observation mode of the endoscope system 1 to the white light observation mode and for setting off the diagnosis assist function of the processor 4, by operating the scope switch 24. Thereafter, the user starts inserting the insertion portion 2a into the body cavity of the subject.

When the control section 43 detects, based on the instruction from the scope switch 24, that the observation mode of the endoscope system 1 is set in the white light observation mode, the control section 43 generates a system control signal for causing white light to be supplied as illumination light to the endoscope 2 and outputs the system control signal to the light source control section 34. When the control section 43 detects, based on the instruction from the scope switch 24, that the diagnosis assist function of the processor 4 is set off, the control section 43 generates a system control signal for causing the image generated by the image generation section 42a to be outputted as an observation image to the display apparatus 5, and outputs the system control signal to the selector 42b and the display control section 42d.

When the observation mode of the endoscope system 1 is set in the white light observation mode, the light source control section 34 performs control on the light emitting section 31 to cause the red light source 31a, the green light source 31b, and the blue light source 31c to be lighted at the same time and to cause the blue light source 31d to be put out, in response to the system control signal outputted from the control section 43. In other words, according to such control by the light source control section 34, during the white light observation mode, white light obtained by combining the R light, the G light, and the BL light is supplied from the light source apparatus 3 to the endoscope 2, the white light is applied onto an object via the illumination lens 21, and an optical image of the object corresponding to reflection light of the white light is picked up by the image pickup device 22c. During the white light observation mode, a white light image corresponding to the optical image picked up by the image pickup device 22c is generated by the image generation section 42a.

When the diagnosis assist function of the processor 4 is set off, the selector 42b performs an action for setting the output destination of the white light image outputted from the image generation section 42a to the display control section 42d, in response to the system control signal outputted from the control section 43.

When the diagnosis assist function of the processor 4 is set off, the display control section 42d performs an action for outputting, as an observation image, the white light image outputted from the image generation section 42a to the display apparatus 5, in response to the system control signal outputted from the control section 43.

The user makes an instruction for setting on the diagnosis assist function of the processor 4 by operating the scope switch 24 in a state where the distal end portion of the insertion portion 2a is placed at a part suspected of existence of a polyp within the body cavity of the subject.

When the diagnosis assist function of the processor 4 is set on and when the observation mode of the endoscope system 1 is set in the white light observation mode, the operation state presumption section 43a, based on the instructions from the scope switch 24, obtains a presumption result that the user observing the image (endoscope image) obtained by picking up the image of the subject by using the endoscope 2 is performing an operation related to search for a polyp.

When the control section 43 detects, based on the presumption result obtained by the operation state presumption section 43a, that the operation related to search for a desired object or a polyp, which is a target of finding, in the subject into which the endoscope 2 is inserted is being performed, the control section 43 generates a system control signal for causing the image in which the specular reflection region is maintained to be outputted as an observation image to the display apparatus 5, and outputs the system control signal to the selector 42b and the display control section 42d.

When the operation related to search for a polyp is being performed, the selector 42b performs an action for setting the output destination of the white light image outputted from the image generation section 42a to the display control section 42d, in response to the system control signal outputted from the control section 43.

When the operation related to search for a polyp is being performed, the display control section 42d performs an action for outputting, as an observation image, the white light image outputted from the image generation section 42a to the display apparatus 5, in response to the system control signal outputted from the control section 43.

The user searches for a polyp existing within the body cavity of the subject by operating the insertion portion 2a while the user is checking the white light image displayed on the display apparatus 5 in a state where the specular reflection region is maintained. When a polyp is found, the user makes an instruction for setting the observation mode of the endoscope system 1 to the narrowband light observation mode by operating the scope switch 24.

When the diagnosis assist function of the processor 4 is set on and when the observation mode of the endoscope system 1 is set in the narrowband light observation mode, the operation state presumption section 43a, based on the instructions from the scope switch 24, obtains a presumption result that the user observing the image (endoscope image) obtained by picking up the image of the subject by using the endoscope 2 is perform ring an operation related to discrimination of a polyp.

When the control section 43 detects, based on the instruction from the scope switch 24, that the observation mode of the endoscope system 1 is set in the narrowband light observation mode, the control section 43 generates a system control signal for causing the G light and the BS light to be supplied as illumination light to the endoscope 2, and outputs the system control signal to the light source control section 34. When the control section 43 detects, based on the presumption result obtained by the operation state presumption section 43a, that the operation related to discrimination of the desired object or the polyp, which is a target of finding, found in the subject into which the endoscope 2 is inserted is being performed, the control section 43 generates a system control signal for causing the image in which the specular reflection region is corrected by the specular reflection region correction section 42c to be outputted as an observation image to the display apparatus 5, and outputs the system control signal to the selector 42b and the display control section 42d.

In response to the system control signal outputted from the control section 43, the light source control section 34 performs control on the light emitting section 31 to cause the green light source 31b and the blue light source 31d to be lighted at the same time and to cause the red light source 31a and the blue light source 31c to be put out in the narrowband light observation mode. In other words, according to such control by the light source control section 34, during the narrowband light observation mode, mix light obtained by combining the G light and the BS light is supplied from the light source apparatus 3 to the endoscope 2, the mix light is applied onto the object via the illumination lens 21, and an optical image of the object corresponding to reflection light of the mix light is picked up by the image pickup device 22c. During the narrowband light observation mode, a narrowband light image corresponding to the optical image picked up by the image pickup device 22c is generated by the image generation section 42a.

When the operation related to discrimination of the polyp is being performed, the selector 42b performs an action for setting the output destination of the image outputted from the image generation section 42a to the specular reflection region correction section 42c, in response to the system control signal outputted from the control section 43.

When the operation related to discrimination of the polyp is being performed, the display control section 42d performs an action for outputting, as an observation image, the image outputted from the specular reflection region correction section 42c to the display apparatus 5, in response to the system control signal outputted from the control section 43.

The user discriminates a grade of malignancy and the like of the polyp found through the above-described operation related to search, by checking the narrowband light image displayed on the display apparatus 5 in a state where the specular reflection region is corrected. After the operation related to discrimination of the polyp is completed, for example, the user makes instructions for setting the observation mode of the endoscope system 1 into the white light observation mode and for setting off the diagnosis assist function of the processor 4, by operating the scope switch 24.

Here, a study conducted by the Applicant has produced a finding that if a specular reflection region is removed from an image obtained when a polyp is searched for, polyp finding rate or polyp detection accuracy is lowered compared to if the specular reflection region is not removed. The study conducted by the Applicant has produced a finding that when a polyp found or detected through search is discriminated, accuracy in determining a grade of malignancy of the polyp can be stabilized by removing a specular reflection region from an image including the polyp. In view of such findings, in the present embodiment, when the diagnosis assist function of the processor 4 is set on, either the observation image in which the specular reflection region is maintained or the observation image in which the specular reflection region is corrected is configured to be selectively outputted to the display apparatus 5, depending on a presumption result obtained by the operation state presumption section 43a. Accordingly, according to the present embodiment, it is possible to reduce a burden on the user who performs diagnosis of a polyp detected by utilizing specular reflection.

Note that when the diagnosis assist function of the processor 4 is set on, the operation state presumption section 43a is not limited to a configuration of presuming an operation state of the user by the presumption method as described above, and the operation state presumption section 43a in the present embodiment may be configured to presume an operation state of the user by using presumption methods as illustrated below.

The operation state presumption section 43a may be configured to obtain a presumption result, for example, by presuming an operation state of the user observing the image (endoscope image) obtained by picking up the image of the subject by using the endoscope 2, based on brightness of the image outputted from the image processing section 42.

More specifically, for example, the operation state presumption section 43a may be configured to calculate an average luminance value of individual pixels included in the image outputted from the image processing section 42, and to obtain the presumption result that the operation of searching for a polyp is being performed if the calculated average luminance value is equal to or higher than a threshold value TH1, but to obtain the presumption result that the operation of discriminating a polyp is being performed if the calculated average luminance value is lower than the threshold value TH1.

The operation state presumption section 43a may be configured to obtain a presumption result, for example, by presuming an operation state of the user observing the image (endoscope image) obtained by picking up the image of the subject by using the endoscope 2, based on a current observation magnification of the endoscope 2 (image pickup portion 22).

More specifically, for example, the operation state presumption section 43a may be configured to obtain a current observation magnification of the endoscope 2 (image pickup portion 22) set based on an instruction from the scope switch 24, and to obtain the presumption result that the operation of searching for a polyp is being performed if the obtained current observation magnification is lower than a threshold value TH2, but to obtain the presumption result that the operation of discriminating a polyp is being performed if the obtained current observation magnification is equal to or higher than the threshold value TH2.

The operation state presumption section 43a may be configured to obtain a presumption result, for example, by presuming an operation state of the user observing the image (endoscope image) obtained by picking up the image of the subject by using the endoscope 2, based on a use state of the treatment instrument 8.

More specifically, for example, the operation state presumption section 43a may be configured to obtain the presumption result that the operation of searching for a polyp is being performed if a distal end portion of the treatment instrument 8 cannot be detected based on a processing result obtained when image recognition processing is performed on the image outputted from the image processing section 42, but to obtain the presumption result that the operation of discriminating a polyp is being performed if the distal end portion of the treatment instrument 8 can be detected. Alternatively, for example, the operation state presumption section 43a may be configured to obtain the presumption result that the operation of searching for a polyp is being performed if an instruction from a predetermined switch provided on the scope switch 24 cannot be detected, but to obtain the presumption result that the operation of discriminating a polyp is being performed if an instruction from the predetermined switch can be detected.

The operation state presumption section 43a may be configured to obtain a presumption result, for example, by presuming an operation state of the user observing the image (endoscope image) obtained by picking up the image of the subject by using the endoscope 2, based on a color tone of the image outputted from the image processing section 42.

More specifically, for example, the operation state presumption section 43a may be configured to extract pixels in a predetermined color (corresponding to a color of a stain solution for polyp) from among the individual pixels included in the image outputted from the image processing section 42, and to obtain the presumption result that the operation of searching for a polyp is being performed if the number of the extracted pixels is smaller than a threshold value TH3, but to obtain the presumption result that the operation of discriminating a polyp is being performed if the number of the extracted pixels is equal to or larger than the threshold value TH3.

The operation state presumption section 43a may be configured to obtain a presumption result, for example, by presuming an operation state of the user observing the image (endoscope image) obtained by picking up the image of the subject by using the endoscope 2, based on a location and a size of a polyp included in the image outputted from the image processing section 42.

More specifically, for example, based on a processing result obtained when image recognition processing and tracking processing are performed on the image outputted from the image processing section 42, if a polyp cannot be detected, or if a polyp exists in a periphery portion of the image, or if the proportion of an area covered by a polyp in the image is less than a threshold value TH4, the operation state presumption section 43a may be configured to obtain the presumption result that the operation of searching for a polyp is being performed. For example, based on the processing result obtained when image recognition processing and tracking processing are performed on the image outputted from the image processing section 42, if a polyp exists in a center part of the image and if the proportion of an area covered by the polyp in the image is equal to or more than the threshold value TH4, the operation state presumption section 43a may be configured to obtain the presumption result that the operation of discriminating a polyp is being performed.

According to the present embodiment, when the operation state presumption section 43a obtains a presumption result by presuming an operation state of the user, any one of the methods illustrated above may be used alone, or two or more of the methods illustrated above may be used in combination. In other words, the operation state presumption section 43a may be configured to presume the operation state, based on at least one of an observation mode used when the subject is observed by using the endoscope 2, brightness of the endoscope image obtained by picking up the image of the subject by using the endoscope 2, an observation magnification used when the subject is observed by using the endoscope 2, a use state of the treatment instrument 8 used when the subject is observed by using the endoscope 2, a color tone of the endoscope image, and a location and a size of a polyp included in the endoscope image.

According to the present embodiment, the diagnosis assist function of the processor 4 may be configured to be set on or off, for example, based on a detection result obtained by detecting whether or not the insertion portion 2a is inserted in the body cavity, instead of the instruction from the polyp diagnosis assist switch of the scope switch 24.

More specifically, for example, the control section 43 (or the operation state presumption section 43a) may be configured to set on the diagnosis assist function of the processor 4 if it is detected, based on brightness and/or a color tone of the image outputted from the image processing section 42, that the insertion portion 2a is inserted in the body cavity, but to set off the diagnosis assist function of the processor 4 if it is detected that the insertion portion 2a is not inserted in the body cavity.

Without limiting to the diagnosis assist function used when diagnosis of a polyp is preformed, the diagnosis assist function in the present embodiment can be used approximately in the same manner, for example, when diagnosis is performed on various abnormalities detected by utilizing specular reflection, such as a metal surface flaw.

More specifically, according to the diagnosis assist function in the present embodiment, for example, it is possible that when the operation state presumption section 43a obtains a presumption result that an operation of searching for a desired object or a metal surface flaw, which is a target of finding, in a subject is being performed, the observation image in which the specular reflection region is maintained is caused to be outputted to the display apparatus 5, and that when the operation state presumption section 43a obtains a presumption result that an operation of discriminating a metal surface flaw found in the subject is being performed, the observation image in which the specular reflection region is corrected by the specular reflection region correction section 42c is caused to be outputted to the display apparatus 5.

Second Embodiment

FIGS. 3 to 7 relate to a second embodiment of the present invention.

Note that in the present embodiment, a detailed description will be omitted with respect to parts having similar configurations, components, and the like to the configurations, components, and the like in the first embodiment, and a description will be given mainly of parts having different configurations, components, and the like from the configurations, components, and the like in the first embodiment.

Figure 3:
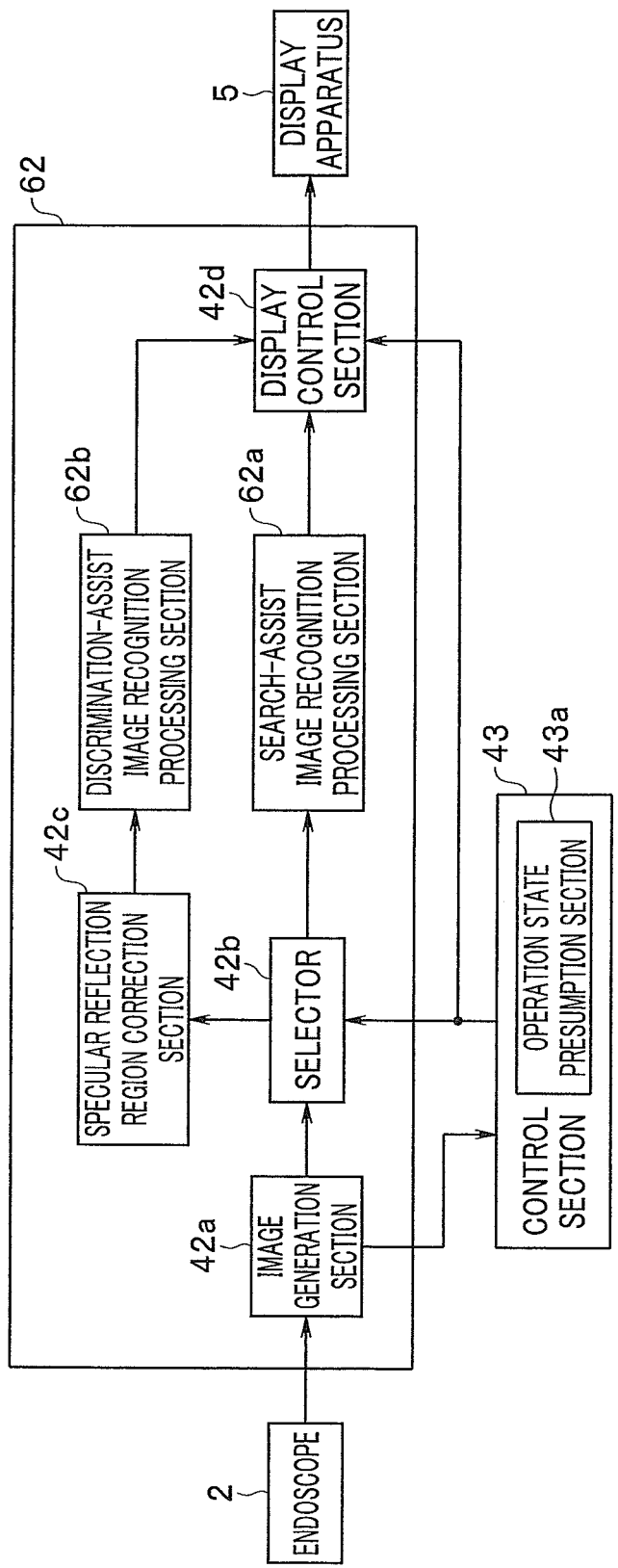
FIG. 3 is a diagram for describing an example of a configuration of an image processing section according to a second embodiment.

A processor 4 in the present embodiment includes an image processing section 62 as illustrated in FIG. 3 in place of the image processing section 42. FIG. 3 is a diagram for describing an example of a configuration of the image processing section according to the second embodiment.

The image processing section 62 is configured with, for example, an image processing circuit. The image processing section 62 includes, for example, the image generation section 42a, the selector 42b, the specular reflection region correction section 42c, the display control section 42d, a search-assist image recognition processing section 62a (hereinafter, abbreviated as the image recognition processing section 62a) provided between an output side of the selector 42b and an input side of the display control section 42d, and a discrimination-assist image recognition processing section 62b (hereinafter, abbreviated as the image recognition processing section 62b) provided between an output side of the specular reflection region correction section 42c and the input side of the display control section 42d, as shown in FIG. 3.

When an operation related to search for a polyp is being performed, the selector 42b is configured to perform an action for setting an output destination of an image outputted from the image generation section 42a to the image recognition processing section 62a, in accordance with a system control signal outputted from the control section 43.

When an operation related to discrimination of a polyp is being performed, the selector 42b is configured to perform an action for setting the output destination of the image outputted from the image generation section 42a to the specular reflection region correction section 42c, in accordance with a system control signal outputted from the control section 43.

The image recognition processing section 62a is configured to perform processing for detecting presence or absence of a polyp in the image outputted via the selector 42b, that is, the image in which a specular reflection region is maintained. When a polyp is detected from the image outputted via the selector 42b, the image recognition processing section 62a is configured to perform processing for generating a detection frame indicating a location and a size of the polyp, and to output the generated detection frame and the image to the display control section 42d. Note that the image recognition processing section 62a in the present embodiment is configured to detect the presence or absence of a polyp and to generate the detection frame by using a convolutional neural network for detection (hereinafter, abbreviated as detection CNN). An example of a configuration and the like of such a detection CNN will be described in detail later.

The image recognition processing section 62b is configured to perform processing for obtaining a classification result by classifying, in accordance with predetermined classification criteria, a polyp included in the image outputted via the selector 42b and the specular reflection region correction section 42c, that is, the image in which the specular reflection region is corrected by the specular reflection region correction section 42c, and to output the obtained classification result and the image to the display control section 42d. Note that the image recognition processing section 62b in the present embodiment is configured to classify a polyp by using a convolutional neural network for classification (hereinafter, abbreviated as classification CNN). An example of a configuration and the like of such a classification CNN will be described in detail later. Hereinbelow, a description will be given by using an example in which the image recognition processing section 62b performs processing for classifying the polyp included in the image in which the specular reflection region is corrected by the specular reflection region correction section 42c, into any one of Type 1, Type 2, and Type 3 of NICE classification. In the present embodiment, the image in which the specular reflection region is corrected is not limited to the image inputted into the image recognition processing section 62b, for example, an image from which a specular reflection region is removed through processing of clipping a rectangle including a polyp from the image outputted from the selector 42b may be configured to be inputted into the image recognition processing section 62b.

When the operation related to search for a polyp is being performed, the display control section 42d performs an action for outputting to the display apparatus 5 an observation image generated by using the image in which the specular reflection region is maintained, which is outputted from the image recognition processing section 62a, and the polyp detection frame, which is the processing result outputted from the image recognition processing section 62a, in accordance with a system control signal outputted from the control section 43.

When the operation related to discrimination of a polyp is being performed, the display control section 42d performs an action for outputting to the display apparatus 5 an observation image generated by using the image in which the specular reflection region is corrected, which is outputted from the image recognition processing section 62b, and the polyp classification result, which is the processing result outputted from the image recognition processing section 62b, in accordance with a system control signal outputted from the control section 43.

When the control section 43 detects, based on a presumption result obtained by the operation state presumption section 43a, that the operation related to search for a polyp is being performed, the control section 43 performs control on the selector 42b and the display control section 42d to cause an observation image corresponding to the processing result obtained through the processing performed by the image recognition processing section 62a on the image in which the specular reflection region is maintained, to be outputted.

When the control section 43 detects, based on a presumption result obtained by the operation state presumption section 43a, that the operation related to discrimination of a polyp is being performed, the control section 43 performs control on the selector 42b and the display control section 42d to cause an observation image corresponding to the processing result obtained through the processing performed by the image recognition processing section 62b on the image in which the specular reflection region is corrected by the specular reflection region correction section 42c, to be outputted.

In other words, according to the action of each section in the present embodiment as described above, for example, when the operation related to search for a polyp is being performed, the observation image including the image in which the specular reflection region is maintained and the detection frame formed around the polyp included in the image is displayed on the display apparatus 5. According to the action of each section in the present embodiment as described above, for example, when the operation related to discrimination of a polyp is being performed, the observation image including the image in which the specular reflection region is corrected and visual information such as a character string for informing the user of which one of Type 1, Type 2, and Type 3 of NICE classification the polyp included in the image belongs to is displayed on the display apparatus 5.

Figure 4:
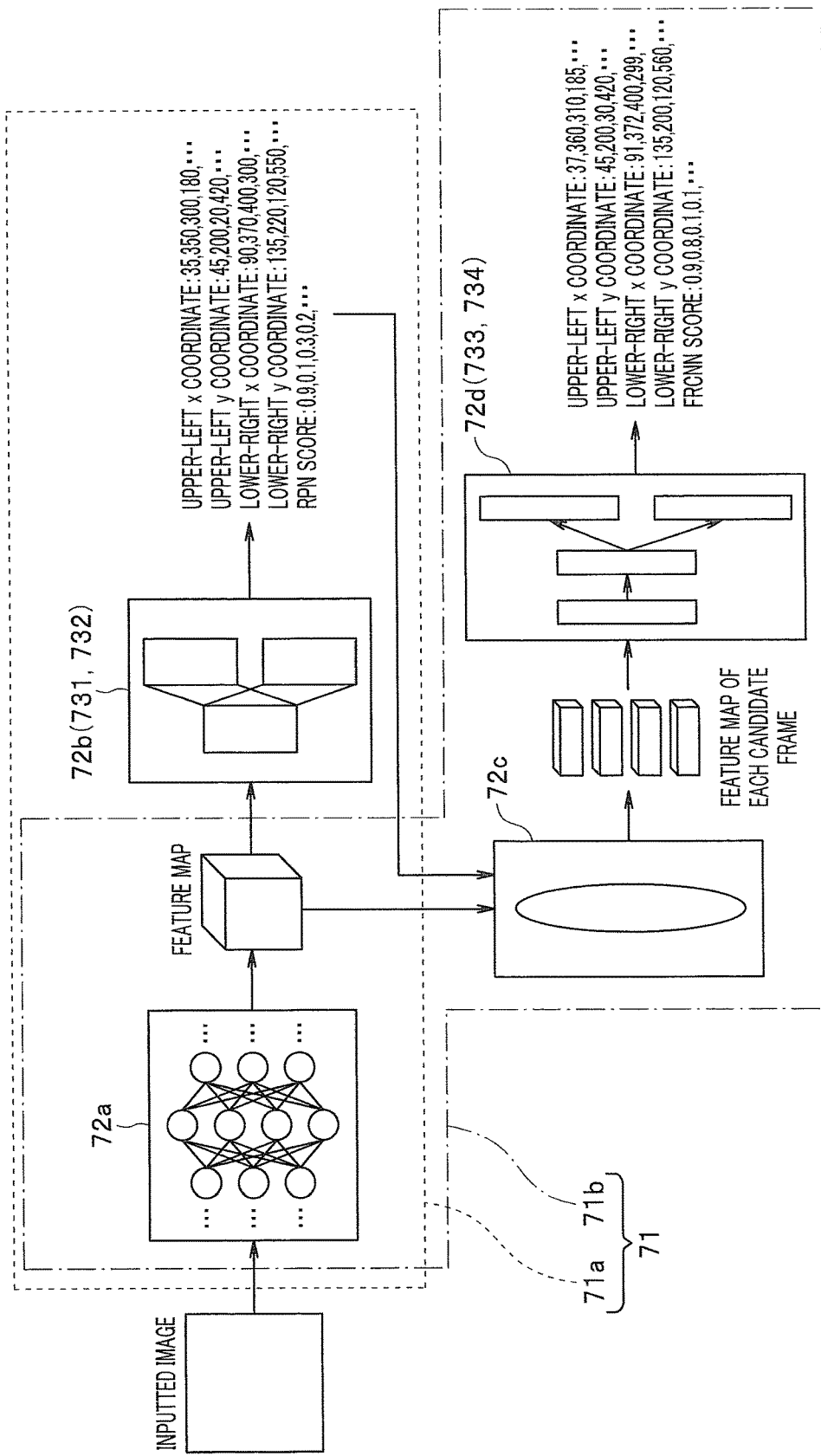
FIG. 4 is a conceptual diagram for describing an example of a configuration and the like of a convolutional neural network for detection used in a search-assist image recognition processing section of the image processing section according to the second embodiment.

Here, an example of the configuration and the like of the detection CNN used in the image recognition processing section 62a will be described with reference to FIG. 4. Note that in the present embodiment, a description will be given by using an example in which Faster R-CNN is used for the detection CNN. FIG. 4 is a conceptual diagram for describing an example of the configuration and the like of the detection CNN used in the search-assist image recognition processing section of the image processing section according to the second embodiment.

As shown in FIG. 4, the detection CNN 71 includes a region proposal network (hereinafter, abbreviated as RPN) 71a configured to detect a rectangular candidate frame including a polyp from the inputted image in which the specular reflection region is maintained, and a fast R-CNN (hereinafter, abbreviated as FRCNN) 71b configured to generate a detection frame by closely examining the polyp included in the detected candidate frame.

As shown in FIG. 4, the RPN 71a includes a feature value extraction CNN 72a and a candidate frame detection CNN 72b. As shown in FIG. 4, the FRCNN 71b includes the feature value extraction CNN 72a, a RoI pooling layer 72c, and a candidate frame classification fully connected layer 72d. In other words, the feature value extraction CNN 72a is shared by both the RPN 71a and the FRCNN 71b.

The feature value extraction CNN 72a is configured to obtain a feature map of the inputted image as an operation result by performing a plurality of convolutional operations and pooling operations on the inputted image. The feature value extraction CNN 72a is configured by using a network structure such as AlexNet or VGG-16.

Note that a description will be given below assuming that the feature value extraction CNN 72a is configured by using VGG-16, unless particularly mentioned otherwise. In other words, a description will be given below assuming that for example, if the inputted image having a horizontal width of W, a vertical width of H, and three channels (red, green, and blue) is inputted into the feature value extraction CNN 72a, a feature map having a horizontal width of W/16, a vertical width of H/16, and 512 channels can be obtained as an operation result by the feature value extraction CNN 72a.

The candidate frame detection CNN 72b is configured, for example, as a three-layer CNN including an RPN frame variation map output convolutional layer 731 configured to obtain and output an RPN frame variation map, and an RPN score map output convolutional layer 732 configured to obtain and output an RPN score map. The candidate frame detection CNN 72b is configured to calculate coordinate values of a candidate frame and an RPN score representing a likelihood of a polyp by performing operations, which will be described later, by using the RPN frame variation map and the RPN score map.

The RPN frame variation map output convolutional layer 731 is configured to obtain and output the RPN frame variation map having, for example, a horizontal width of W/16, a vertical width of H/16, and 4×A channels by performing operations using the feature map obtained as the operation result by the feature value extraction CNN 72a. In other words, the RPN frame variation map is obtained as a map in which locations in spatial directions correspond to locations in the inputted image and which includes frame variation amounts (an amount of movement of a frame center and an amount of magnification of a frame width in each of xy directions) of each anchor in a channel direction. Note that the above value A is assumed to represent the number of anchors. An anchor is assumed to represent a shape of a candidate frame including an aspect ratio and a scale.

The RPN score map output convolutional layer 732 is configured to obtain and output the RPN score map having, for example, a horizontal width of W/16, a vertical width of H/16, and 2×A channels by performing operations using the RPN frame variation map outputted from the RPN frame variation map output convolutional layer 731. In other words, the RPN score map is obtained as a map in which the locations in the spatial directions correspond to the locations in the inputted image and which includes scores (a polyp score and a background score) of each anchor in the channel direction.

Here, when (0, 0) is a center of a rectangular candidate frame represented by an anchor a, coordinate values of the rectangular candidate frame (x coordinate and y coordinate of an upper-left corner of a rectangle and x coordinate and y coordinate of a lower-right corner of the rectangle) can be calculated by using a following equation (1). Note that in the following equation (1), it is assumed that b represents a size of an anchor base, r represents an aspect ratio, and s represents a scale. In the following equation (1), it is assumed that R represents the number of aspect ratios, S represents the number of scales, and the relation R×S=A is true.

$$a_{S \times i+j} = \left( \frac{b}{2} - \frac{b \cdot s_j}{\sqrt{r_i}}, \frac{b}{2} - b \cdot s_j \sqrt{r_i}, \frac{b}{2} + \frac{b \cdot s_j}{\sqrt{r_i}}, \frac{b}{2} + b \cdot s_j \sqrt{r_i} \right) \quad (1)$$

$$(0 \leq i < R, 0 \leq j < S)$$

The candidate frame detection CNN 72b calculates coordinate values p of a candidate frame by performing operations using a following equation (2).

$$p_{x,y,n} = \left( cx - \frac{w}{2}, cy - \frac{h}{2}, cx + \frac{w}{2}, cy + \frac{h}{2} \right) \quad (2)$$

$$\left( 0 \leq x < \frac{W}{16}, 0 \leq y < \frac{H}{16}, 0 \leq n < A \right)$$

Note that each parameter included in the above equation (2) is calculated by using following equations (3) to (11), respectively. It is assumed that bmap in the following equations (3) to (6) indicates an RPN frame variation map.

$$dx = bmap(x, y, 4 \times n + 0) \quad (3)$$

$$dy = bmap(x, y, 4 \times n + 1) \quad (4)$$

$$dw = bmap(x, y, 4 \times n + 2) \quad (5)$$

$$dh = bmap(x, y, 4 \times n + 3) \quad (6)$$

$$p^{temp} = (16 \times x + a_{n,0}, 16 \times y + a_{n,1}, 16 \times x + a_{n,2}, 16 \times y + a_{n,3}) \quad (7)$$

$$cx = dx \times (p_2^{temp} - p_0^{temp}) + \frac{p_0^{temp} + p_2^{temp}}{2} \quad (8)$$

$$cy = dy \times (p_3^{temp} - p_1^{temp}) + \frac{p_1^{temp} + p_3^{temp}}{2} \quad (9)$$

$$w = e^{dw} \times (p_2^{temp} - p_0^{temp}) \quad (10)$$

$$h = e^{dh} \times (p_3^{temp} - p_1^{temp}) \quad (11)$$

The candidate frame detection CNN 72b calculates an RPN score sc representing a likelihood of a polyp by performing operations using a following equation (12). It is assumed that smap in the following equation (12) indicates an RPN score map.

$$sc_{x,y,n} = \frac{e^{smap(x,y,2 \times n+0)}}{e^{smap(x,y,2 \times n+0)} + e^{smap(x,y,2 \times n+1)}} \quad (12)$$

$$\left( 0 \leq x < \frac{W}{16}, 0 \leq y < \frac{H}{16}, 0 \leq n < A \right)$$

The RoI pooling layer 72c is configured to clip a feature map for each candidate frame by using the feature map obtained as the operation result by the feature value extraction CNN 72a and the coordinate values of each candidate frame obtained as the operation result by the candidate frame detection CNN 72b, and to resize each of the clipped feature maps through max pooling. The RoI pooling layer 72c is configured to obtain and output a feature map having, for example, a horizontal width of 7, a vertical width of 7, and 512 channels as a feature map of each candidate frame.

The candidate frame classification fully connected layer 72d is configured, for example, as a four-layer CNN including an FRCNN frame variation map output fully connected layer 733 configured to obtain and output an FRCNN frame variation map, and an FRCNN score map output fully connected layer 734 configured to obtain and output an FRCNN score map. The candidate frame classification fully connected layer 72d is configured to calculate coordinate values of a detection frame and an FRCNN score representing a likelihood of a polyp by performing operations similar to the operations shown as the above equations (1) to (12) by using the FRCNN frame variation map and the FRCNN score map.

The FRCNN frame variation map output fully connected layer 733 is configured to obtain and output the FRCNN frame variation map having, for example, a horizontal width of 1, a vertical width of 1, M clipped maps, and 4 (respective amounts of movement of the frame center and respective amounts of magnification of the frame widths in the xy directions)×A channels by performing operations using the feature map obtained as the operation result by the feature value extraction CNN 72a.

The FRCNN score map output fully connected layer 734 is configured to obtain and output the FRCNN score map having, for example, a horizontal width of 1, a vertical width of 1, M clipped maps, and 2 (a polyp score and a background score)×A channels by performing operations using the FRCNN frame variation map outputted from the FRCNN frame variation map output fully connected layer 733.

Figure 5:
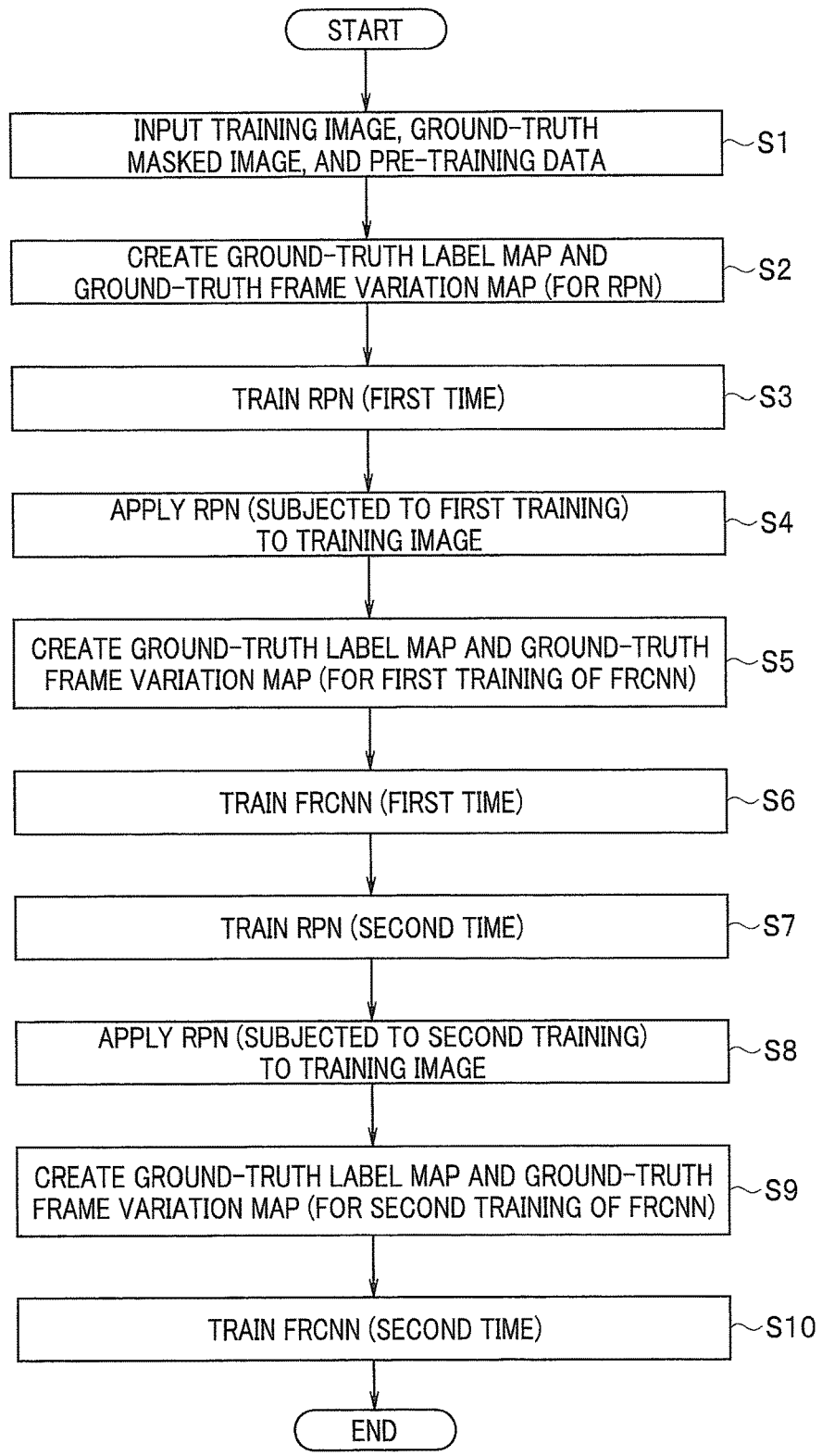
FIG. 5 is a flowchart for describing an example of a procedure of training the convolutional neural network for detection in FIG. 4.

Next, an example of a procedure of training the detection CNN 71 will be described with reference to FIG. 5. Note that in the present embodiment, a description will be given by using an example in which after each of the RPN 71a and the FRCNN 71b is trained one time, each of the RPN 71a and the FRCNN 71b is further trained one time while the feature value extraction CNN 72a is fixed, whereby the feature value extraction CNN 72a is shared by both the RPN 71a and the FRCNN 71b. In the present embodiment, it is assumed that for example, an endoscope image obtained by picking up the image of an inside of a body cavity by using an endoscope is used as a training image. In the present embodiment, it is assumed that for example, an image in which a polyp region in the above training image is colored white and a background region (a region other than the polyp region) in the above training image is colored black is used as a ground-truth masked image. FIG. 5 is a flowchart for describing the example of the procedure of training the convolutional neural network for detection in FIG. 4.

In step S1 of FIG. 5, a training image, a ground-truth masked image, and pre-training data are inputted into the RPN 71a.

Note that the pre-training data inputted in the processing in step S1 of FIG. 5 is data obtained beforehand by training the RPN 71*a* by using images included in a large image database such as ImageNet.

In step S2 of FIG. 5, a ground-truth frame variation map and a ground-truth label map for training the RPN 71*a* are created by using the ground-truth masked image inputted through the processing in step S1 of FIG. 5.

Note that the ground-truth frame variation map created through the processing in step S2 of FIG. 5 is created as a map having, for example, a horizontal width of W/16, a vertical width of H/16, and 4 (respective amounts of movement of the frame center and respective amounts of magnification of the frame widths in the xy directions)×A channels. The ground-truth label map created through the processing in step S2 of FIG. 5 is created as a map having, for example, a horizontal width of W/16, a vertical width of H/16, and 1 (a label)×A channels. In the processing in step S2 of FIG. 5, for example, if an overlapping rate of coordinate values of a candidate frame corresponding to each point in the map with the ground-truth masked image is equal to or more than 50%, a label=0 indicating polyp is stored in the ground-truth label map, but if the overlapping rate is equal to or more than 0% and less than 50%, a label=1 indicating background is stored in the ground-truth label map. In the processing in step S2 of FIG. 5, when the label=0 is stored in the ground-truth label map, an amount of variation from the candidate frame to a rectangle bounding a polyp region in the ground-truth masked image is stored in the ground-truth frame variation map.

In step S3 of FIG. 5, first training of the RPN 71*a* is performed by using the training image inputted through the processing in step S1 of FIG. 5 and the ground-truth frame variation map and the ground-truth label map created through the processing in step S2 of FIG. 5.

Note that in the processing in step S3 of FIG. 5, the pre-training data inputted in step S1 of FIG. 5 is used for an initial value for the feature value extraction CNN 72*a*. The processing in step S3 of FIG. 5 is performed to optimize both the feature value extraction CNN 72*a* and the candidate frame detection CNN 72*b*. In the processing in step S3 of FIG. 5, it is assumed that a result of weighting and adding a softmax cross entropy between the ground-truth label map and the RPN score map and a smooth L1 loss between the ground-truth frame variation map and the RPN frame variation map is used for a loss function. In the processing in step S3 of FIG. 5, it is assumed that the feature value extraction CNN 72*a* and the candidate frame detection CNN 72*b* are optimized by using stochastic gradient descent (SGD).

In step S4 of FIG. 5, coordinate values of each candidate frame and an RPN score representing a likelihood of a polyp are calculated individually by applying the RPN 71*a* subjected to the first training, which is built through the processing in step S3 of FIG. 5, to the training image inputted through the processing in step S1 of FIG. 5.

In step S5 of FIG. 5, a ground-truth frame variation map and a ground-truth label map for first training of the FRCNN 71*b* are created by using the coordinate values of the candidate frames calculated through the processing in step S4 of FIG. 5 and the ground-truth masked image inputted through the processing in step S1 of FIG. 5.

Note that the ground-truth frame variation map created through the processing in step S5 of FIG. 5 is created as a map having, for example, a horizontal width of W/16, a vertical width of H/16, M outputted candidate frames, and 4 (respective amounts of movement of the frame center and respective amounts of magnification of the frame widths in the xy directions)×A channels. The ground-truth label map created through the processing in step S5 of FIG. 5 is created as a map having, for example, a horizontal width of W/16, a vertical width of H/16, M outputted candidate frames, and 1 (a label)×A channels. In the processing in step S5 of FIG. 5, for example, if an overlapping rate of the coordinate values of a candidate frame calculated through the processing in step S4 of FIG. 5 with the ground-truth masked image is equal to or more than 50%, the label=0 indicating polyp is stored in the ground-truth label map, but if the overlapping rate is equal to or more than 0% and less than 50%, the label=1 indicating background is stored in the ground-truth label map. In the processing in step S5 of FIG. 5, when the label=0 is stored in the ground-truth label map, an amount of variation from the candidate frame to the rectangle bounding the polyp region in the ground-truth masked image is stored in the ground-truth frame variation map.

In step S6 of FIG. 5, first training of the FRCNN 71*b* is performed based on the training image inputted through the processing in step S1 of FIG. 5 and the ground-truth frame variation map and the ground-truth label map created through the processing in step S5 of FIG. 5.

Note that in the processing in step S6 of FIG. 5, the pre-training data inputted in step S1 of FIG. 5 is used for an initial value for the feature value extraction CNN 72*a*. The processing in step S6 of FIG. 5 is performed to optimize both the feature value extraction CNN 72*a* and the candidate frame classification fully connected layer 72*d*. In the processing in step S6 of FIG. 5, a loss function and an optimization method similar to the loss function and the optimization method used in the processing in step S3 of FIG. 5 are used.

In step S7 of FIG. 5, second training of the RPN 71*a* is performed by using the training image inputted through the processing in step S1 of FIG. 5 and the ground-truth frame variation map and the ground-truth label map created through the processing in step S2 of FIG. 5.

Note that in the processing in step S7 of FIG. 5, it is assumed that the feature value extraction CNN 72*a* is fixed at a result of the first training of the FRCNN 71*b*, which is obtained through the processing in step S6 of FIG. 5. The processing in step S7 of FIG. 5 is performed to optimize only the candidate frame detection CNN 72*b*.

In step S8 of FIG. 5, coordinate values of each candidate frame and an RPN score representing a likelihood of a polyp are calculated by applying the RPN 71*a* subjected to the second training, which is built through the processing in step S7 of FIG. 5, to the training image inputted through the processing in step S1 of FIG. 5.

In step S9 of FIG. 5, a ground-truth frame variation map and a ground-truth label map for second training of the FRCNN 71*b* are created by using the coordinate values of the candidate frames calculated through the processing in step S8 of FIG. 5 and the ground-truth masked image inputted through the processing in step S1 of FIG. 5.

In step S10 of FIG. 5, second training of the FRCNN 71*b* is performed by using the training image inputted through the processing in step S1 of FIG. 5 and the ground-truth frame variation map and the ground-truth label map created through the processing in step S9 of FIG. 5.

Note that in the processing in step S10 of FIG. 5, it is assumed that the feature value extraction CNN 72*a* is fixed at the result of the first training of the FRCNN 71*b*, which is obtained through the processing in step S6 of FIG. 5. The processing in step S7 of FIG. 5 is performed to optimize only the candidate frame classification fully connected layer 72*d*.

In other words, the image recognition processing section 62a in the present embodiment is configured to detect presence or absence of a polyp in the image outputted via the selector 42b (the image in which the specular reflection region is maintained) and to generate a detection frame indicating a location and a size of the detected polyp by using the detection CNN 71 built through the series of training procedure illustrated in FIG. 5.

Figure 6:
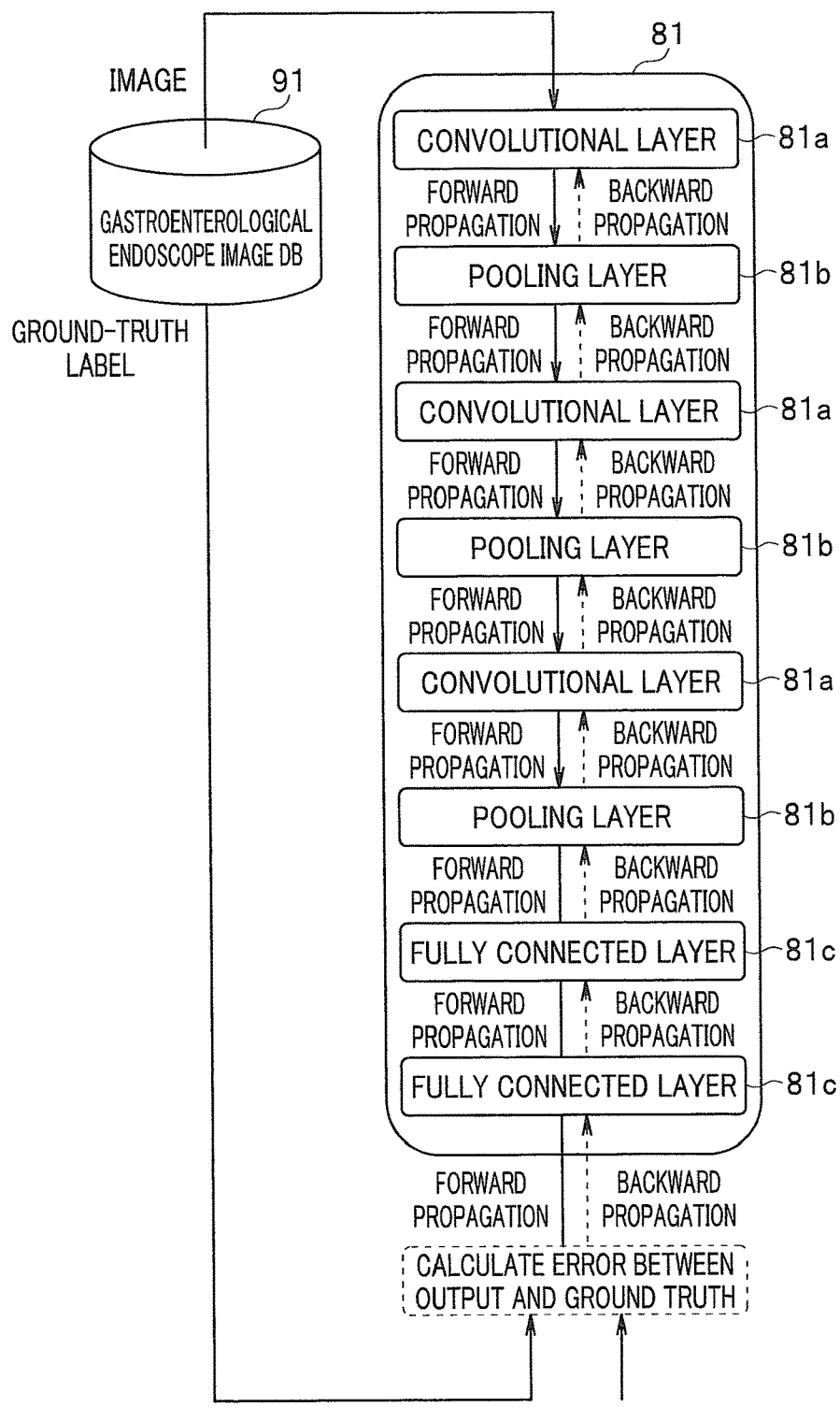
FIG. 6 is a conceptual diagram for describing an example of a configuration and the like of a convolutional neural network for classification used in a discrimination-assist image recognition processing section of the image processing section according to the second embodiment.

Next, an example of the configuration and the like of the classification CNN used in the image recognition processing section 62b will be described with reference to FIG. 6. FIG. 6 is a conceptual diagram for describing an example of the configuration and the like of the convolutional neural network for classification used in the discrimination-assist image recognition processing section of the image processing section according to the second embodiment.

As shown in FIG. 6, the classification CNN 81 is configured to obtain a classification result by classifying a polyp included in an inputted image in accordance with NICE classification, by iterating processing by convolutional layers 81a and pooling layers (subsampling layers) 81b three times on the inputted image in which the specular reflection region is corrected, and thereafter further performing processing by two fully connected layers 81c.

Note that it is assumed that each convolutional layer 81a of the classification CNN 81 is configured to output to the subsequent pooling layer 81b a processing result obtained by applying a nonlinear function (ReLU) after convolution processing. In the classification CNN 81, it is only necessary that the processing by the convolutional layers 81a and the pooling layers 81b performed on the inputted image be iterated at least once. In the classification CNN 81, it is only necessary that at least one fully connected layer 81c be included.

In the present embodiment, the classification CNN 81 can be built by using AlexNet, ZFNet, VGG-16, GoogLeNet, Network in Network, or the like. Accordingly, a description will be given below of an example in which the classification CNN 81 is built by using VGG-16.

In the classification CNN 81 built using VGG-16, a convolution filter with a size of 3×3 is used, and a processing result of convolution of the inputted image with the convolution filter is applied to the nonlinear function ReLU. In the classification CNN 81 built using VGG-16, after processing by convolutional layers is consecutively performed two or three times, max pooling (subsampling for selecting a maximum value of 2×2 outputs of a previous layer) is performed (note that in VGG-16, a pooling is not counted for the number of layers). In the classification CNN 81 built using VGG-16, after the processing by 13 convolutional layers and five max poolings are performed, processing by three fully connected layers is performed.

Next, an example of a procedure of training the classification CNN 81 will be described.

In the training of the classification CNN 81, for example, an endoscope image such as a white light image or a narrowband light image stored in a gastroenterological endoscope image database (hereinafter, abbreviated as the gastroenterological endoscope image DB) 91 outside the endoscope system 1 can be used. When the training of the classification CNN 81 is performed, for example, a training data set is used, which is data obtained by combining an endoscope image and a label generated by classifying the endoscope image in accordance with NICE classification, into one set.

In the training of the classification CNN 81, for example, if several tens of thousands of the above training data sets can be prepared, the VGG-16 network can be directly trained. However, if a sufficient number of the above training data sets cannot be prepared, for example, fine tuning using a data set including a gastroenterological endoscope image may be configured to be performed on the VGG-16 network on which pre-training has been performed by using a large image DB such as ImageNet.

In the training of the classification CNN 81, when an image included in the above training data set is inputted, convolution and pooling are iteratively performed on the inputted image, whereby a signal propagates in a forward direction (from an input side to an output side), a difference between the signal from an output layer and a teacher signal is calculated as an error, and then as the signal propagates in a backward direction (from the output side to the input side) so that the calculated error is reduced, a weight at each layer is updated. When the training of the classification CNN 81 is completed, the weight at each layer is fixed.

For example, if an unknown image is inputted into the trained classification CNN 81, convolution and pooling are iteratively performed on the inputted image, whereby a signal propagates in the forward direction, and the inputted image is classified based on each signal value outputted from the output layer (fully connected layer). More specifically, for example, three signal values corresponding to the three labels Type 1, Type 2, and Type 3 of NICE classification respectively are outputted from the output layer (fully connected layer) of the classification CNN 81, and a label indicating a maximum value of the three signal values is obtained as a classification result.

In other words, the image recognition processing section 62b in the present embodiment is configured to obtain a classification result by classifying a polyp included in the image outputted via the selector 42b and the specular reflection region correction section 42c (the image in which the specular reflection region is corrected by the specular reflection region correction section 42c) in accordance with NICE classification by using the classification CNN 81 built by the method as described above.

As described above, according to the present embodiment, even if the processor 4 is configured with provision of the image processing section 62 in place of the image processing section 42, operations and effects similar to the operations and effects of the first embodiment can be demonstrated.

Note that according to the present embodiment, for example, while the image recognition processing section 62b is configured using the classification CNN 81, the image recognition processing section 62a may be configured using a convolutional neural network for extracting a region (hereinafter, abbreviated as region extraction CNN) in place of the detection CNN 71.

For example, the region extraction CNN is configured to obtain region extraction results by extracting a normal region and a region in which a polyp exists from the image outputted via the selector 42b (the image in which the specular reflection region is maintained), to perform processing of consolidating the obtained region extraction results, to perform processing of correcting the specular reflection region in the image including the consolidated region, and to perform classification according to NICE classification (Type 1, Type 2, or Type 3) by inputting the image subjected to the processing into the classification CNN.

Figure 7:
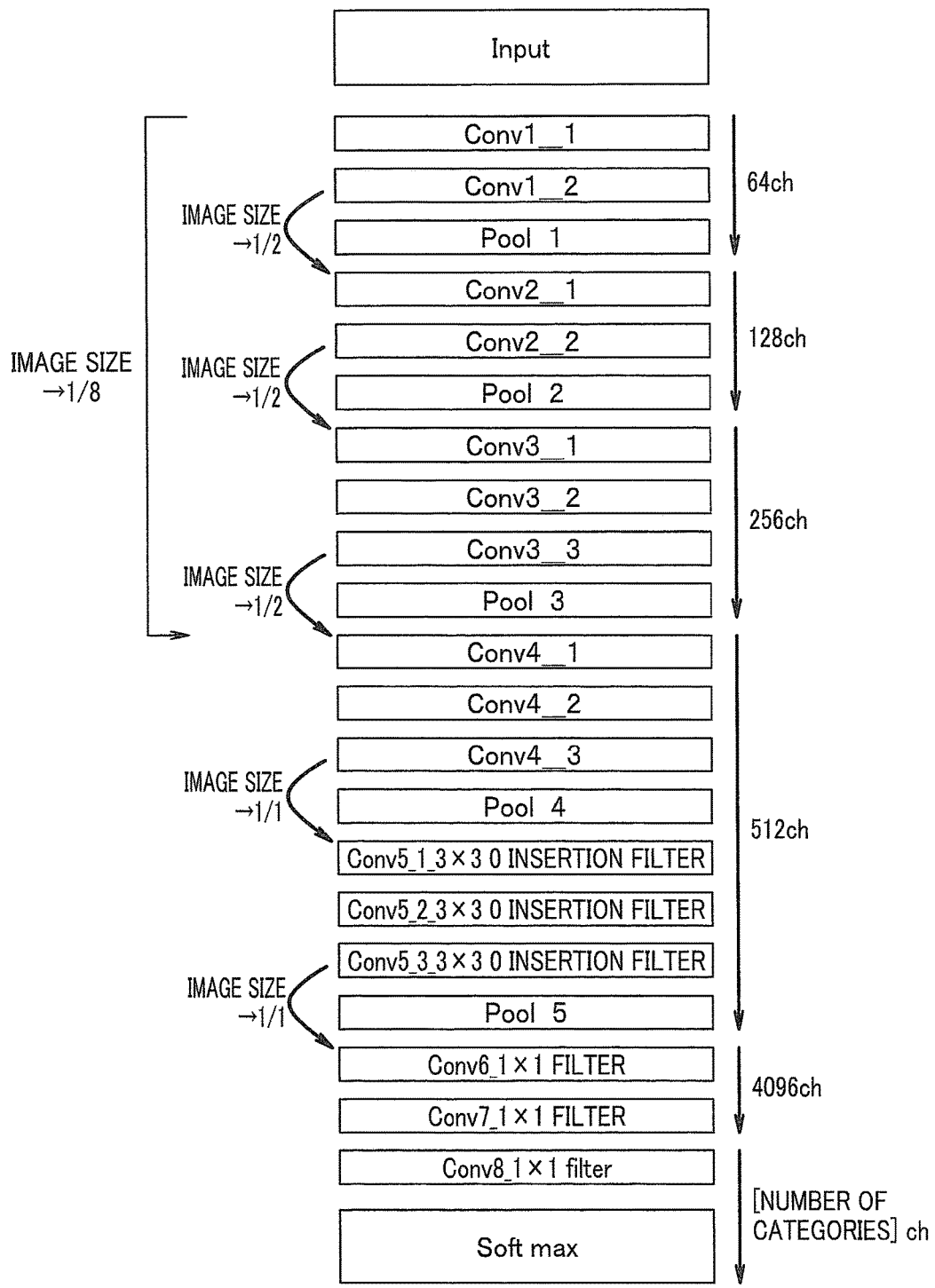
FIG. 7 is a diagram showing an example of a network configuration included in DeepLab system.

Here, a description will be given below of an example of a configuration and the like of the region extraction CNN using DeepLab system including a network configuration as shown in FIG. 7. FIG. 7 is a diagram showing an example of the network configuration included in the DeepLab system.

In the DeepLab system, an inputted image is inputted into a CNN (more specifically, an adjusted model of VGG-16), a score map (representing a likelihood of a predetermined category) having ⅛ of vertical and horizontal image sizes of the respective inputted image is outputted for each category, and resolution conversion is performed in such a manner that each outputted score map becomes an image having the same sizes as the inputted image through bilinear interpolation. Then, processing related to conditional random field (more specifically, fully connected CRF) is performed on the inputted image and the score maps subjected to the resolution conversion, whereby an image representing which category each pixel belongs to is outputted.

As diversion of a CNN for classifying an image by category to a CNN for extracting a region of a category, for example, a fully convolutional network (FCN) is proposed, which is configured to allow a probability of a category outputted from an output layer to include spatial information, by replacing all fully connected layers with convolutional layers. In the DeepLab system, the FCN is introduced as an adjusted model of VGG-16.

As shown in FIG. 7, in the adjusted model of VGG-16, an output from the output layer is configured to have ⅛ of the sizes of an inputted image, by adjusting a stride at fourth and fifth poolings included in the VGG processing from 2 to 1, and replacing all three fully connected layers with convolutional layers. At a convolutional layer immediately after the fourth pooling at which the stride is adjusted from 2 to 1, filter characteristics and locations of sampled pixels of the image on an input side are configured to match by making an interval of sampling pixels on an input side of the filter twice as long as an original interval. Similarly, an interval of sampling pixels on an input side of a convolutional layer immediately after the fifth pooling is made four times as long as the original interval. Since the outputted score map of the adjusted model of VGG-16 has ⅛ of the sizes of the inputted image, the processing related to fully connected CRF is performed after resolution conversion is performed to allow the outputted score map to have the same sizes as the inputted image through bilinear interpolation.

In the DeepLab system, since the spatial information included in the outputted score map of the adjusted model of VGG-16 has low resolution, the processing related to fully connected CRF is performed on the outputted score map, whereby high-precision region extraction in a unit of a pixel is configured to be performed. Fully connected CRF is configured to output a category map according to an input of the inputted image and the score map subjected to the resolution conversion. Fully connected CRF estimates a category of each pixel included in the inputted image by performing iterative processing using unary potential based on a likelihood of a category obtained from the score map and pairwise potential based on an indicator indicating "whether a similar color exists in vicinity", which is calculated among all pixels of the inputted image, and on an indicator indicating "smoothness of a category region".

According to the present embodiment, for example, while the image recognition processing section 62a is configured using the detection CNN 71, the image recognition processing section 62b may be configured using the above-described region extraction CNN in place of the classification CNN 81. Note that in such a configuration, it is preferable that the image from which the specular reflection region is removed through processing of clipping a rectangle including a polyp in the image outputted from the selector 42b be inputted into the image recognition processing section 62b.

According to the present embodiment, for example, functions of both the image recognition processing sections 62a and 62b may be implemented by modifying the above-described detection CNN 71 as appropriate. More specifically, for example, the RPN 71a and the FRCNN 71b are configured to include different feature value extraction CNNs, and when search for a polyp is being performed, the image in which the specular reflection region is maintained is configured to be inputted into the feature value extraction CNN of the RPN 71a, and when discrimination of a polyp is being performed, the image in which the specular reflection region is corrected by the specular reflection region correction section 42c is configured to be inputted into the feature value extraction CNN of the FRCNN 71b.

Note that the present invention is not limited to each of the above-described embodiments and, needless to say, various changes and applications can be made without departing from the scope of the invention.

What is claimed is:

1. An image processing apparatus comprising a processor, wherein the processor is configured to: obtain a presumption result by presuming an operation state of a user who performs an operation while the user observes an image obtained by picking up an image of a subject;
   perform processing for correcting a specular reflection region included in the image obtained by picking up the image of the subject; and
   when detecting, based on the presumption result, that a first operation related to search for a desired object in the subject is performed, perform control for causing the image in which the specular reflection region is maintained to be outputted as an observation image, and when detecting that a second operation related to discrimination of the desired object found in the subject is performed, perform control for causing the image in which the specular reflection region is corrected to be outputted as the observation image.

2. The image processing apparatus according to claim 1, wherein the processor presumes the operation state of the user who performs the operation while the user observes an endoscope image that is the image obtained by picking up the image of the subject by using an endoscope.

3. The image processing apparatus according to claim 2, wherein the processor presumes the operation state based on at least one of an observation mode used when the subject is observed by using the endoscope, brightness of the endoscope image, an observation magnification used when the subject is observed by using the endoscope, a use state of an observation assist instrument used when the subject is observed by using the endoscope, a color tone of the endoscope image, and a location and a size of the desired object included in the endoscope image.

4. The image processing apparatus according to claim 1, wherein when detecting, based on the presumption result, that the first operation is performed, the processor performs control for causing the observation image corresponding to a processing result obtained by performing first image recognition processing for detecting presence or absence of the desired object on the image in which the specular reflection region is maintained, to be outputted, and when detecting that the second operation is performed, performs control for causing the observation image corresponding to a processing result obtained by performing second image recognition processing for classifying the desired object in accordance with predetermined classification criteria on the image in which the specular reflection region is corrected, to be outputted.

5. The image processing apparatus according to claim 4, wherein the first image recognition processing is performed by using a convolutional neural network.

6. The image processing apparatus according to claim 4, wherein the second image recognition processing is performed by using a convolutional neural network.

7. An image processing method comprising:

obtaining a presumption result by presuming an operation state of a user who performs an operation while the user observes an image obtained by picking up an image of a subject;

performing processing for correcting a specular reflection region included in the image obtained by picking up the image of the subject; and when detecting, based on the presumption result, that a first operation related to search for a desired object in the subject is performed, performing control for causing the image in which the specular reflection region is maintained to be outputted as an observation image, and when detecting that a second operation related to discrimination of the desired object found in the subject is performed, performing control for causing the image in which the specular reflection region is corrected to be outputted as the observation image.

\* \* \* \* \*